United States Patent [19]

Schachar

[11] 4,440,477

[45] Apr. 3, 1984

[54] METHOD AND DEVICE FOR MEASURING THE OPTICAL POWER OF THE CORNEA

[76] Inventor: Ronald A. Schachar, Denison, Tex.

[21] Appl. No.: 316,664

[22] Filed: Oct. 30, 1981

[51] Int. Cl.³ ........................... A61B 3/10; A61B 3/14
[52] U.S. Cl. ..................................... 351/212; 351/206
[58] Field of Search ............... 351/212, 211, 221, 214, 351/206; 354/62

[56] References Cited

U.S. PATENT DOCUMENTS 4,159,867 7/1979 Achatz ................................ 351/212

*Primary Examiner*—John K. Corbin
*Assistant Examiner*—Rodney B. Bovernick

*Attorney, Agent, or Firm*—Jerry W. Mills; Gregory M. Howison; Nina Medlock

[57] ABSTRACT

A method and device for measuring the optical power of the cornea is provided. The device comprises a light source to illuminate the cornea, apparatus for forming a profile image of the cornea, apparatus for measuring the actual image distance from the anterior corneal surface, processing apparatus for calculating the radius of curvature and dioptric power of the cornea and display apparatus for displaying the calculated data. The method of the present invention comprises illuminating the cornea with a light source, forming a profile image of the cornea, measuring the actual image distance from the anterior corneal surface and calculating the anterior radius of curvature and dioptric power of the cornea.

21 Claims, 2 Drawing Figures

METHOD AND DEVICE FOR MEASURING THE OPTICAL POWER OF THE CORNEA

TECHNICAL FIELD

This invention relates to a method and device for measuring the optical power of the cornea. More specifically, the device and method utilize the actual, not calculated, image distance from the anterior corneal surface to calculate the radius of curvature and dioptric power of the cornea.

BACKGROUND ART

Present methods of measuring the optical power of the cornea actually involve calculating the image distance and radius of curvature of the cornea. This is usually accomplished by using an instrument called a keratometer. Keratometers, the most common of which are made by Bausch & Lomb, American Optical, Keller, Haig Strait and Terry Operating Keratometer, project an image of a known size onto the cornea and the size of the reflected image is measured to determine the magnification (actually minification since the cornea is convex). Because the object is a known distance from the anterior corneal surface, the image distance can be calculated. The radius of curvature of the anterior corneal surface can then be calculated and the dioptric power of the cornea determined.

The basic assumption in calculating the corneal radius of curvature by keratometry is that the anterior corneal surface is a perfectly corrected optical surface. The cornea, however, is not a perfect optical surface and, in fact, is rather irregular. An imperfectly corrected optical system like the normal anterior surface of the cornea will not actually have a focal point, but a circle of least confusion, i.e., the cornea has spherical aberration. As a result, standard keratometers will give an incorrect radius of curvature for the cornea, and in general, will give a steeper radius of curvature than the actual radius of curvature of the cornea. This concept is important in understanding the optical power of the cornea following refractive techniques such as radial keratotomy, epikeratophakia, keratophakia, and keratomileusis, and probably accounts for many of the inaccuracies obtained when using formulas to determine intraocular lens power.

Immediately following radial keratotomy and other refractive procedures, the cornea becomes an even more imperfect optical system, and the error in calculating the image distance and radius of curvature of the cornea will be even larger. To determine the actual effective optical power of the cornea (effective optical radius of curvature), the image distance must actually be measured, not calculated. A need exists, therefore, for a method and device for measuring the actual image distance from the anterior corneal surface.

DISCLOSURE OF THE INVENTION

In accordance with the present invention, a method and apparatus for directly measuring the image distance from the anterior corneal surface are provided. The measured (not calculated) image distance is then used to determine the effecive optical radius of curvature of the anterior corneal surface. Then, an accurate measure of the effective power of the cornea can be obtained.

The method of the present invention comprises illuminating the cornea with a light source, measuring the actual image distance from the anterior corneal surface, calculating the anterior radius of curvature of the cornea and then calculating the dioptric power of the cornea.

The device of the present invention comprises an illuminating apparatus to illuminate the cornea of the eye, and a processor for measuring the image distance from the anterior corneal surface and calculating the anterior radius of curvature and dioptric power of the cornea. The illuminating apparatus is preferably a high intensity light source, such as a slit lamp.

In accordance with the preferred embodiment, an apparatus for forming a profile image of the illuminated cornea is provided. This image forming apparatus is, for example, a camera which photographs a profile image of the cornea from which the processor can measure the actual image distance. To avoid the necessity for developing film and save time, a video camera is used as the image forming apparatus. The profile image is fed into the processor which digitizes the image, measures the image distance from the anterior corneal surface, and then calculates the anterior radius of curvature and dioptric power of the cornea. Further in accordance with the preferred embodiment, an apparatus for displaying the calculated data is provided. The display apparatus can be any display board and can be positioned such that the data is displayed within a microscopic field of a microscope having oculars such that the data can be viewed by looking through the oculars of the microscope.

DETAILED DESCRIPTION

Figure 1:
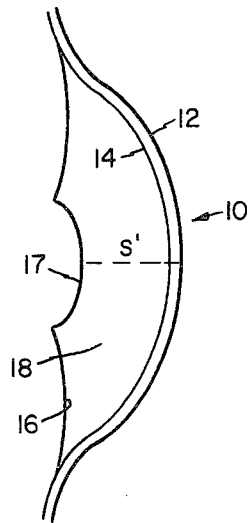
FIG. 1 is a profile representation of the cornea.

Referring now to FIG. 1, a profile representation of the cornea 10 is shown. The image distance is represented by a dotted line s' extending from the anterior corneal surface 12 to the lens 17. The internal corneal surface 14, iris 16 and anterior chamber 18 are also illustrated.

Because the cornea is not a perfectly corrected optical system, the measured image distance will not be the same as the calculated image distance using a keratometer. As noted earlier, kerotometers project an image of a known size onto the cornea and the size of the reflected image is measured to determine the magnification (actually minification since the cornea is convex), m. By having the object a known distance from the anterior corneal surface, s, the image distance, s', can be calculated from the formula:

$$m = -\frac{s'}{s} \tag{1}$$

where
 m = magnification,
 s' = image distance, and
 s = object distance.

The radius of curvature of the anterior corneal surface, r, can then be calculated by using the standard formula for mirrors:

$$\frac{1}{s} + \frac{1}{s'} = -\frac{2}{r} \tag{2}$$

The dioptric power of the cornea can then be determined from the formula:

$$D = \frac{n-1}{r} \quad (3)$$

where
D = dioptric power of the cornea,
n = index of refraction of the cornea, and
r = radius of curvature of the anterior corneal surface.

Formula (1), however, only holds for a perfectly corrected optical system. Since the corneal surface is rather irregular, the calculated image distance will not be accurate and will, therefore, lead to the calculation of an erroneous radius of curvature and dioptric power of the cornea.

In accordance with the present invention, formula (1) is avoided by actually measuring the image distance from the anterior corneal surface. In the preferred embodiment the distance of the catoptric image from the anterior corneal surface is measured. The radius of curvature can then be obtained directly using formula (2) and the dioptric power calculated using formula (3).

Figure 2:
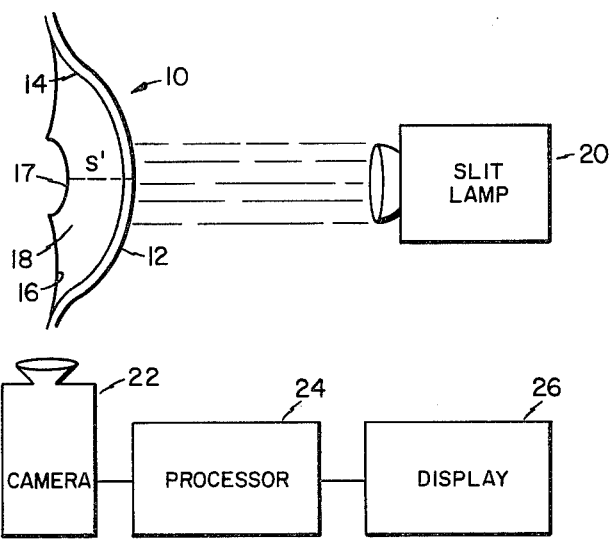
FIG. 2 is a schematic illustration of the preferred system for performing the present invention.

Referring now to FIG. 2, a schematic illustration of the preferred system for performing the present invention is shown. The cornea 10 is illuminated by a light source 20. Camera 22 photographs a profile image of the illuminated cornea and processor 24 measures the actual image distance, s', from the anterior corneal surface 12. Once the image distance, s', has been measured the anterior radius of curvature can be calculated manually, but the processor 24 is preferably programmed to perform the necessary calculations. It is understood that the image distance is to be measured from the center of the cornea and servo mechanisms can be used to detect the center of the cornea. Light source 20 is preferably a slit lamp. To avoid the necessity for developing film, camera 22 is preferably a video camera which feeds a profile image of the cornea 10 directly to the processor 24.

Further in accordance with the preferred embodiment, a display board 26 is provided to display the calculated radius of curvature and dioptric power of the cornea. Display board 26 can be located within a microscopic field of a microscope having oculars such that the calculated data can be viewed while looking through the oculars of the microscope.

Whereas the invention has been described with respect to preferred embodiments, it is apparent to one skilled in the art that various modifications will now be apparent and such are intended to be within the scope of the appended claims.

What is claimed is:

1. A device for measuring the optical power of the cornea, comprising:
    means for illuminating the cornea with light from an object disposed a known distance from the anterior surface of the cornea; and
    means for forming an optical representation of a cross section of the cornea and means for directly measuring from said optical representation the distance from the anterior corneal surface to the image formed by light from the object passing through the corneal surface such that the radius of curvature of the anterior surface of the cornea can be calculated.

2. The device as recited in claim 1 further comprising means for calculating the anterior radius of curvature and dioptric power of the cornea using the predetermined object distance and the measured image distance.

3. The device as recited in claim 2 further comprising means for displaying the calculated anterior radius of curvature and dioptric power of the cornea.

4. The device as recited in claim 1 wherein the means for illuminating the cornea is a slit lamp.

5. The device as recited in claim 1 wherein the means for measuring the image distance from the anterior corneal surface comprises:
    means for forming a profile image of the illuminated cornea from which the actual image distance from the anterior corneal surface to the image formed interior thereto can be measured.

6. The device as recited in claim 5 wherein the image forming means comprises a video camera disposed at an angle with respect to the illuminating ray with the image formed on the surface of the lens of the eye such that the catoptic image can be detected.

7. The device as recited in claim 5 wherein the means for measuring the image distance from the anterior corneal surface further comprises a processor which measures the image distance from the profile image of the cornea.

8. The device as recited in claim 7 wherein the processor also calculates the anterior radius of curvature and dioptric power of the cornea.

9. The device as recited in claim 3 wherein the display means is a video display board.

10. The device as recited in claim 3 wherein the display means are located in a microscopic field of a microscope having oculars such that the calculated radius of curvature and dioptric power of the cornea can be viewed by looking through the oculars.

11. A method for measuring the optical power of the cornea, comprising:
    illuminating the cornea with light from an object disposed a predetermined distance from the anterior surface of the cornea;
    forming an optical representation of a cross section of a cornea;
    using said optical representation to measure the actual distance from the anterior corneal surface to the image formed interior to the corneal surface; and
    calculating the anterior corneal radius of curvature and dioptric power of the cornea from the predetermined distance object and the measured image distance.

12. The method as recited in claim 11 further comprising displaying the calculated anterior radius of curvature and dioptric power of the cornea on a display board for viewing.

13. The method as recited in claim 11 wherein a slit lamp is used to illuminate the cornea and form a catoptic image on the surface of the lens of the eye.

14. The method as recited in claim 11 further comprising forming a profile image of the cornea by a video camera.

15. The method as recited in claim 14 wherein the image distance from the anterior corneal surface is measured by a processor which measures the image distance from the profile image of the cornea.

16. The method as recited in claim 15 wherein the processor also calculates the anterior radius of curvature and dioptric power of the cornea.

17. The method as recited in claim 12 wherein the claculated anterior radius of curvature and dioptric power of the cornea are displayed on a video display board.

18. The method as recited in claim 12 wherein the calculated anterior radius of curvature and dioptric power of the cornea are displayed in a microscopic field of a microscope having oculars such that the calculated radius of curvature and dioptric power of the cornea can be view by looking through the oculars.

19. The method as recited in claim 11 wherein a photoelectric cell is used to measure the image distance from the anterior corneal surface.

20. A method for measuring the optical power of the cornea, comprising:
   illuminating the cornea with a slit lamp to form a catoptic image interior to the anterior corneal surface;
   forming an optical representation of a cross section of the cornea and means for directly measuring from said optical representation;
   using said optical representation to measure the actual distance of the catoptic image from the anterior corneal surface; and
   calculating the anterior radius of curvature of the cornea with the formula:

$$\frac{1}{s} + \frac{1}{s'} = \frac{2}{4}$$

where s is the distance from the anterior corneal surface to the illuminator of the slit lamp, s' is the measured catoptic image distance and r is the radius of curvature of the anterior corneal surface.

21. The method of claim 20 further comprising calculating the dioptric power by the formula:

$$D = \frac{n-1}{r}$$

where D is the dioptric power and n is the index of refraction of the medium interior to the cornea.

* * * * *